(12) United States Patent
Desai (10) Patent No.: US 10,335,121 B2
(45) Date of Patent: Jul. 2, 2019

(54) FEMALE URINATION RECEIVER

(71) Applicant: Akhil Rajendra Desai, Tongaat (ZA)

(72) Inventor: Akhil Rajendra Desai, Tongaat (ZA)

( * ) Notice: Subject to any disclaimer, the term of this patent is extended or adjusted under 35 U.S.C. 154(b) by 854 days.

(21) Appl. No.: 14/471,417

(22) Filed: Aug. 28, 2014

(65) Prior Publication Data

US 2014/0371628 A1 Dec. 18, 2014

Related U.S. Application Data

(63) Continuation-in-part of application No. PCT/ZA2012/000012, filed on Feb. 28, 2012.

(51) Int. Cl.
| | | |
|---|---|---|
| *A61F 5/44* | (2006.01) | |
| *A61B 10/00* | (2006.01) | |
| *A61F 5/455* | (2006.01) | |

(52) U.S. Cl.
CPC ............ *A61B 10/007* (2013.01); *A61F 5/455* (2013.01); *A61F 5/4556* (2013.01)

(58) Field of Classification Search
CPC ....... A61B 10/007; A61F 5/455; A61F 5/4556
USPC .......................................................... 604/329
See application file for complete search history.

(56) References Cited

U.S. PATENT DOCUMENTS

| | | | | |
|---|---|---|---|---|
| 3,774,455 A | * | 11/1973 | Seidler | G01N 33/493 422/549 |
| 3,894,845 A | * | 7/1975 | McDonald | A61B 10/007 422/430 |
| 4,815,151 A | | 3/1989 | Ball | |
| 5,368,583 A | * | 11/1994 | Fleury | A61B 5/20 600/573 |
| 5,422,076 A | | 6/1995 | Jones | |
| 6,027,490 A | * | 2/2000 | Radford | A61M 1/0001 220/770 |
| 6,299,606 B1 | * | 10/2001 | Young | A61B 10/007 604/317 |
| 6,409,971 B1 | * | 6/2002 | Wilkinson | G01N 27/123 422/83 |
| 2003/0149408 A1 | * | 8/2003 | Levinson | A61B 10/007 604/329 |
| 2003/0203375 A1 | * | 10/2003 | Kelly | C07K 14/47 435/6.16 |
| 2007/0185465 A1 | * | 8/2007 | Campbell | A61F 5/451 604/347 |
| 2007/0259442 A1 | * | 11/2007 | Gould | A61B 10/007 436/165 |

FOREIGN PATENT DOCUMENTS

| | | |
|---|---|---|
| CN | 101583316 A | 11/2009 |
| JP | 3861189 B2 | 10/2006 |
| WO | 2005089687 | 9/2005 |

OTHER PUBLICATIONS

International Search Report dated Oct. 29, 2012, corresponding to PCT/ZA2012/000012.

* cited by examiner

*Primary Examiner* — Andrew J Mensh
(74) *Attorney, Agent, or Firm* — Young & Thompson (57) ABSTRACT

A receiver for urine whether for taking sample or disposing thereof, includes an open-topped of saddle shape which approximates the configuration of thighs, labia or other convenient zone.

20 Claims, 8 Drawing Sheets

FEMALE URINATION RECEIVER

TECHNICAL FIELD OF THE INVENTION

This invention relates to a receiver for urine samples and also to a female urination receiver.

BACKGROUND ART

Urine is an important diagnostic tool for measuring health and well-being of patients. The clinical information obtained from a urine specimen is influenced by the collection method, timing and handling.

A midstream clean catch Specimen is the preferred type of specimen for culture and sensitivity testing because of the reduced incidence of cellular and microbial contamination.

However, despite the importance of urine samples, their method of collection is very seldom conducted within the required protocols of hygiene and sterility.

In fact, urine samples are generally obtained by direct urination into a sample bottle or via a jug or the like into such a bottle with neither the jug nor the sample bottle being stored under sterile conditions. The collection of the sample may be accompanied by spillage or overflow and is generally unhygienic.

Furthermore, urine samples obtained in this way generally include the initial flow of excreted urine, which may not be as representative a sample as a sample from the middle of an excretion. The initial sample may include bacteria or other microorganisms that are not actually present in the urine. It is preferable to obtain a mid-stream urine flow for the purposes of obtaining more precise results.

Due to the above identified problems, even the simple dipstick tests conducted in a Doctors Surgery room can yield unreliable results.

In addition to the above, there is also a need for a urinating receiver that conforms to the shape of the female anatomy, and that can be used in a variety of instances, where access to a lavatory is limited. For example, during a long motorcar trip or even on a walking trip, or for Post-operative conditions as well as incontinence which provide serious difficulties for female sufferers.

It is an object of this invention to provide a urine receiver that, at least partially, alleviates some of the above mentioned problems.

DISCLOSURE OF THE INVENTION

According to the invention a urine receiver essentially for females is provided which includes an open top of saddle shape which at least approximates the configuration of the inside of the thighs, labia, or other convenient zone.

The receiver may be provided with a handle such as a jug handle as well as a spout for easy disposing of the contents.

The receiver may also have a closable outlet located in the base for discharge of the contents, or for collecting samples of urine.

The outlet closure may include a retractable plug.

A sample container may be attachable to the outlet for collecting the urine sample.

The sample container and the outlet may comprise a bayonet joint so that the sample container may be easily connected and disconnected from the receiver.

The bayonet joint is comprised of one or more protrusions located about the outer circumference of the lower end of the receiver, on one hand, and a channel formed proximal to the upper end of the sample container. The channel may further include one or more transverse grooves, preferably two transverse grooves. The protrusions accordingly engage not only the channel itself but also the transverse grooves, thereby ensuring that the sample container not only remains connected to the receiver, but also ensuring that the sample container is not rotated past a specific point, engagement with the grooves providing a positive indication of required steps in the attachment of the sample container to the receiver.

Connection of the sample container to the outlet of the receiver may cause the plug to be retracted into an open position, allowing the urine to drain into the sample container.

The sample container may be a special purpose sterile container, sealed by a membrane that is pierced on connection of the container to the receiver. Alternatively, and in another embodiment of the invention the sample container may be a standard, non sterile sample bottle. The sample container may additionally include a lid for sealing the container once the sample has been obtained.

The sample container may be fully inserted from the bottom of the receiver. Once inserted, the membrane will be pierced, and this may be identifiable by a positive clicking sound, which would be the protrusion of the receiver engaging the groove of the channel of the bayonet joint. This engagement may resist the sample container from being removed from the receiver without adequate force. At this point the protrusion of the receiver is engaged in the first groove in the channel of the bayonet joint. The sample container may then be rotated, causing the membrane to be cut approximately half way around the opening of the sample container. This may be again identifiable by a further positive clicking sound, being the protrusions of the receiver engaging a further groove in the channel of the bayonet joint. At this point the protrusion of the receiver is engaged in the second groove in the channel of the bayonet joint. This engagement may resist the further rotation of the sample container. The sample container may then be inserted further into the receiver and the membrane will be cut further.

A sample can now be taken, and the sample container lies at the outlet of the receiver. Pressure applied to the sample container will allow for the sample container to be filled by the urine collected in the receiver. The sample container is pushed against the retractable plug and a spring is activated to allow for the plug to open and urine begins to fill into the sample container. When pressure is released, the spring will bias the retractable plug into the original closed position and urine will stop flowing from the receiver.

The sample container may then be removed by twisting it in the opposite direction as to insertion.

Alternatively, the sample container may be connected to the outlet by a threaded screw connection.

The sample container includes a cross member which breaks the surface tension of the sample and this prevents any drops from being left behind once the sample container is removed from the receiver.

In order to provide instant pH and other pertinent detection, the receiver may include a holder for litmus or other indicators, and a suitable spillage protector for the spout.

The holder may include channels located along the interior wall of the receiver, alternatively the holder may include a separate insert receivable in the receiver. The insert may be shaped to additionally support a filter and/or sponge conforming in shape to the inside of the receiver, for absorbing the initial stream of urine and prevent unwanted ingress of microorganisms or other dirt.

The sponge may be constructed of cellulose or other absorbable material.

The insert may be located on a ledge extending around the interior of the receiver and may include a solid base sloping towards an aperture through which the urine not absorbed by the sponge, may flow.

The walls of the receiver may be transparent to allow the indicator strip to be viewed without removing it from the receiver.

A replaceable rim element adapted to fit the rim and to form a seal with the zone during use, may also be provided.

The rim element may be flexible as well as compressible so that it can seal well with a minimum of pressure being applied.

This avoids, or at least minimises soiling of the user's hands, clothes and surrounding floor, furniture and the like.

Where the receiver is to be used by various different users over a period of time, a new rim element may be provided for each new user, thus improving hygienic conditions.

A support base may be provided, on which the receiver may be located when not in use.

BRIEF DESCRIPTION OF THE DRAWINGS

An embodiment of the invention is described below with reference to the accompanying drawings, in which.

DETAILED DESCRIPTION OF THE PREFERRED EMBODIMENT

In the drawings, a receiver 10 includes a saddle-shaped opening 12 with a rim 14. The receiver includes a pouring spout 20 and a handle 22.

A lid 16 is also provided to seal the receiver 10 and prevent spillage or contamination of the contents during the time lapse between providing the sample and testing of the sample.

The receiver 10 is mounted on a support base 18 by a bayonet joint so that it is easily attached and removed when necessary.

Figure 1:
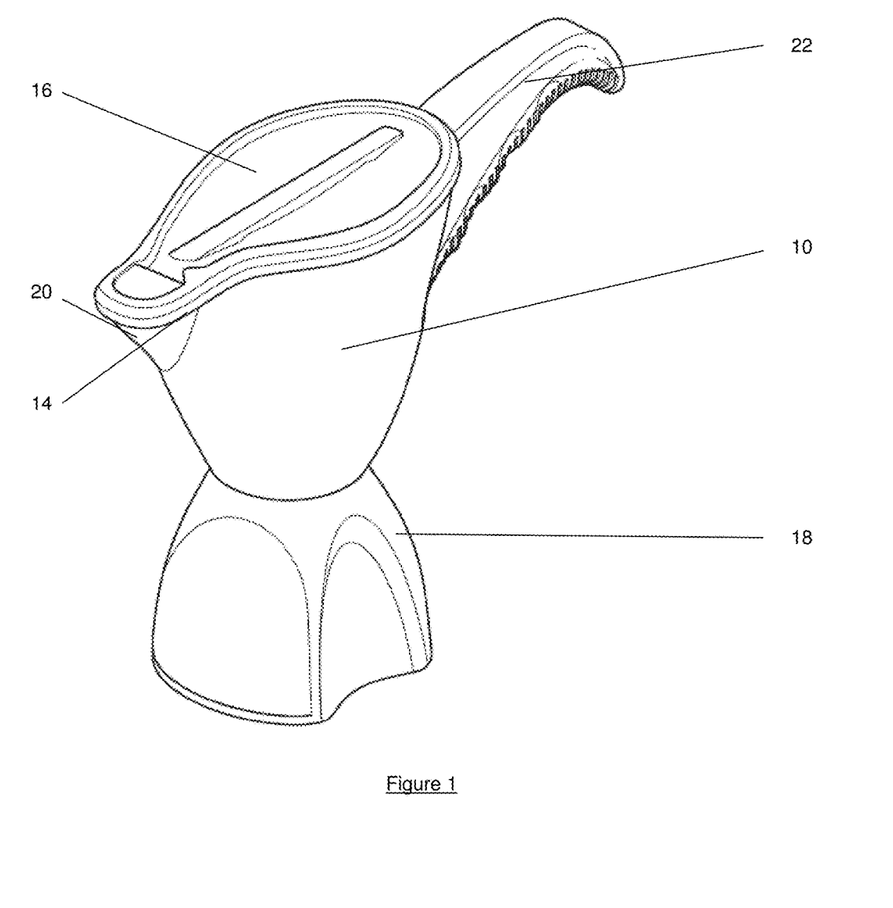
FIG. 1 is an isometric projection of the receiver including the lid and support base.
Figure 2:
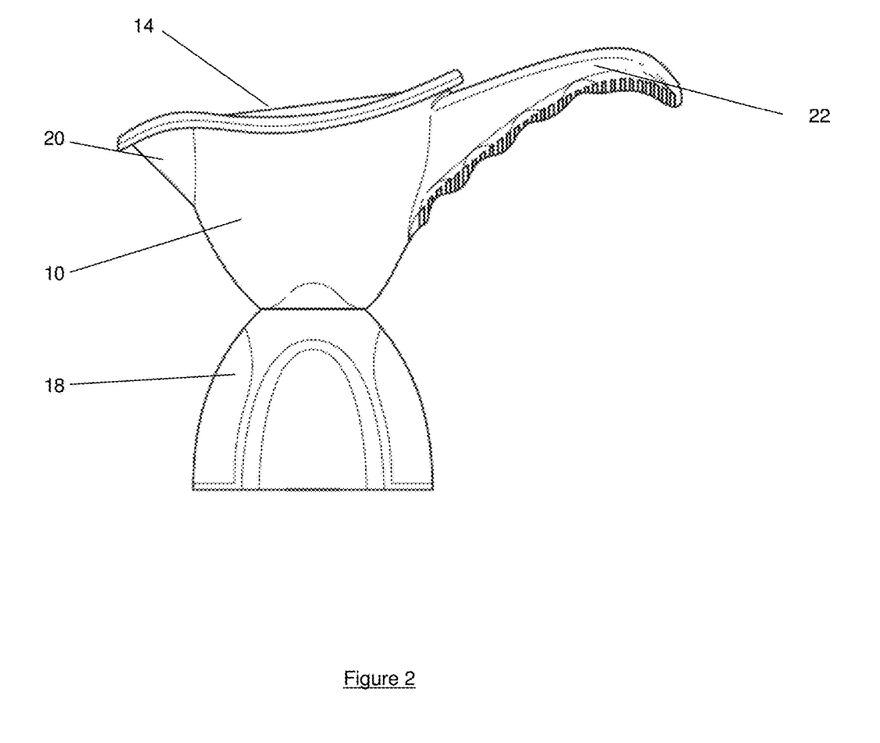
FIG. 2 is a side view of the receiver located on the support base.
Figure 3:
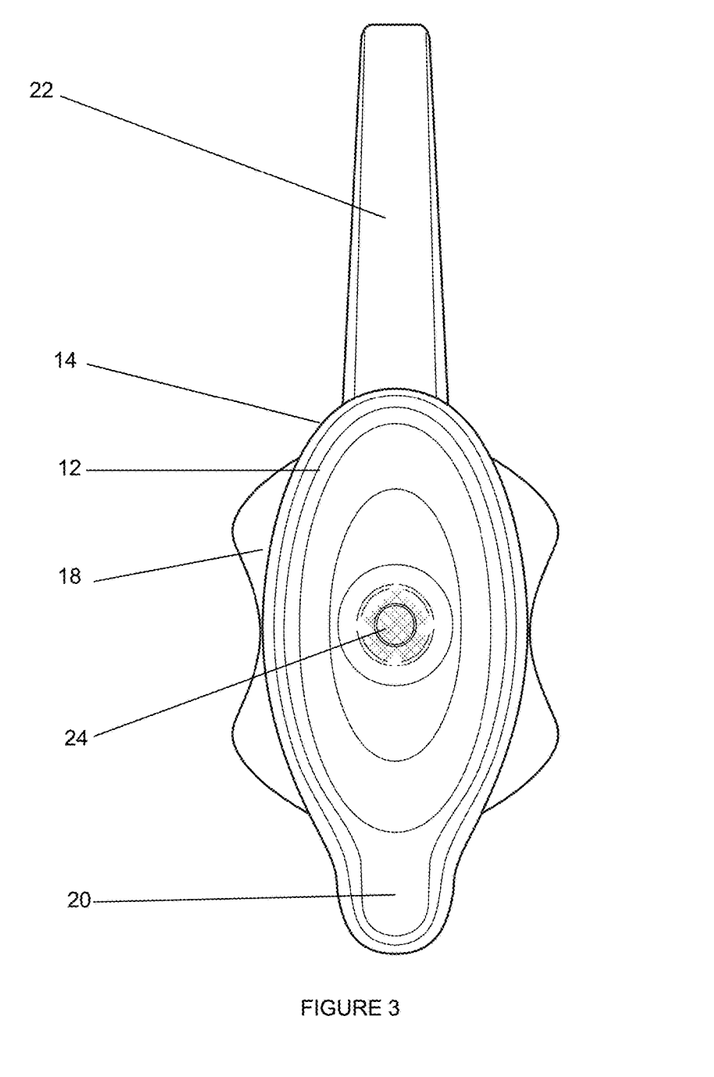
FIG. 3 is a top view of the receiver according to the invention.
Figure 4:
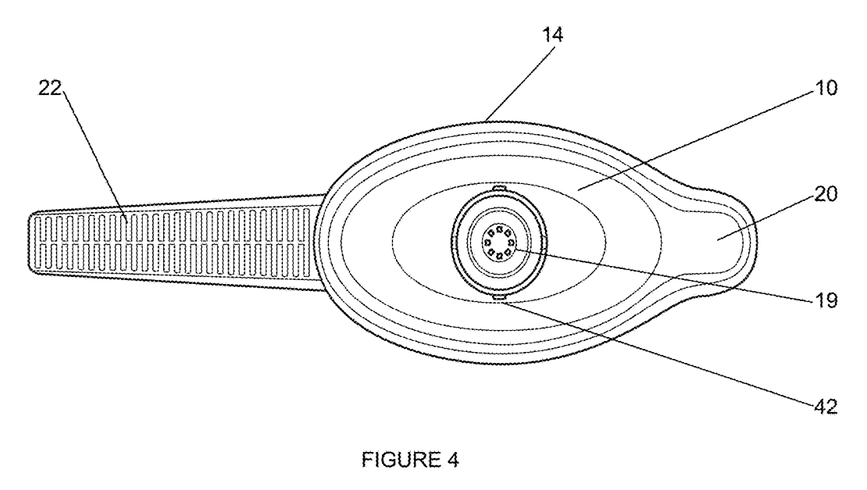
FIG. 4 is a bottom view.

Referring to FIGS. 3 and 4, an outlet 19 is located at the base of the receiver 10, for draining the urine away.

The outlet 19 includes a plug 24 biased in the closed position by a spring (not shown) and openable from the exterior of the receiver 10.

Figure 5:
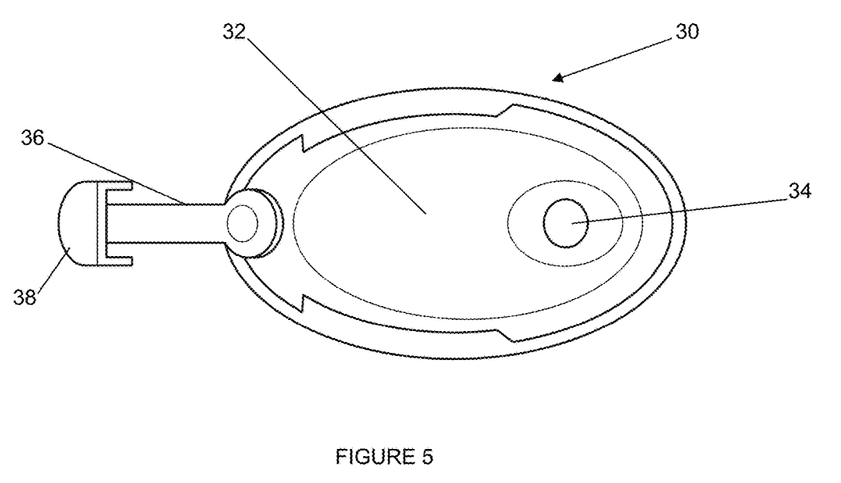
FIG. 5 is a top view of the filter/sponge insert.

Referring to FIG. 5, an insert 30 for supporting a filter pad and/or sponge (not shown) is removably located inside the receiver 10, referring to FIG. 5, the insert includes a solid base 32, that slopes towards an aperture 34, through which the overflow urine (mid-stream urine) may flow, once the initial drops of urine have been absorbed by the sponge/filter (not shown). The insert additionally includes a channel shaped extension 36 for receiving an indicator strip, commonly referred to as a "dip stick" such as litmus. The insert includes a spillage protector 38 for covering the spout opening.

Figure 6:
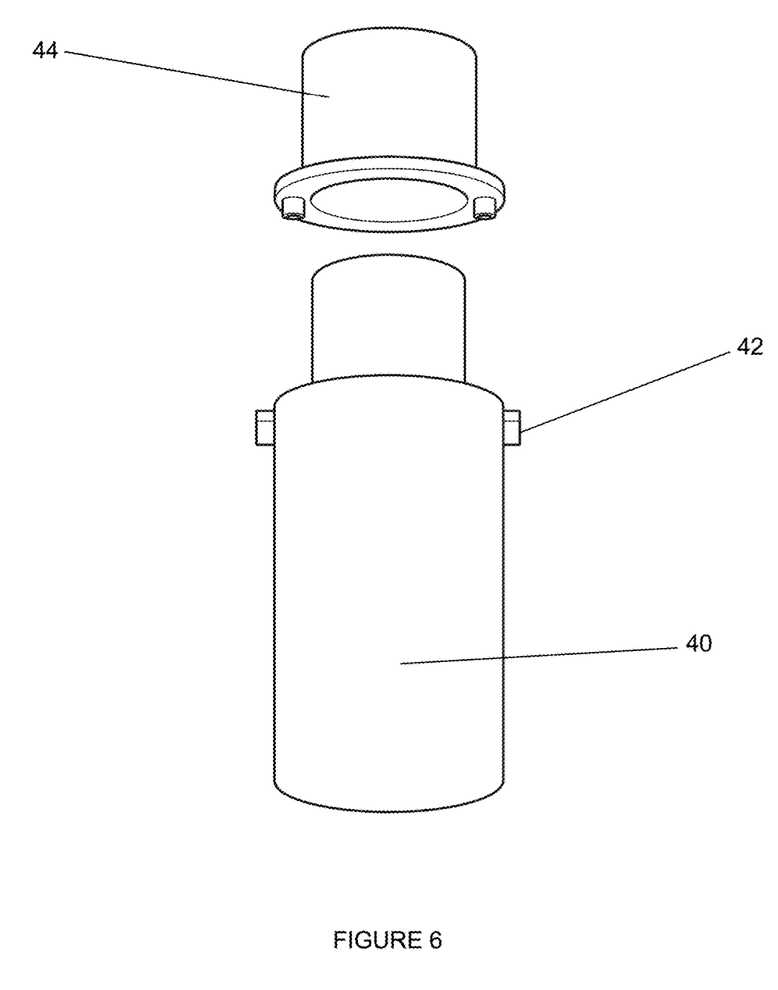
FIG. 6 is a view of a sample bottle for use with the receiver.

Referring to FIG. 6, a sample container 40 is attachable to the receiver outlet 16 for collecting the urine sample. The container 40 and the outlet 19 comprise a bayonet joint indicated by reference 42 so that the sample container may be easily connected and disconnected to and from the receiver.

The bayonet joint 42 comprises a channel 66 with various transverse grooves 68 located in the channel. The channel 66 typically includes two transverse grooves 68. The transverse grooves 68 of the channel 66 engage protrusions 70 defined by the receiver 10, thereby ensuring that the sample container 40 remains in a connected state to the receiver 10 and furthermore, ensuring that the sample container 40 is not rotated past a specific point.

In an alternative embodiment of the invention (not shown) the sample container may be connected to the outlet by a threaded screw connection.

Connection of the sample container 40 to the outlet 19 causes the plug 24 to be pushed up into an open position, allowing the urine to drain into the sample container 40.

In this embodiment of the invention, the sample container 40 is a special purpose sterile container, sealed by a membrane (not shown) that is pierced on connection of the container to the receiver 10. The sample container additionally includes a rubber lid 44 for sealing the container once the sample has been obtained.

Alternatively, and in another embodiment of the invention the sample container may be a standard, non sterile sample bottle.

A rim element (not shown) that has the same shape as the rim and has a channel to engage the rim may be removably located on the rim 12. The element includes a channel that fits over the rim 12 of the receiver.

The element is both flexible and compressible so that an excellent seal is achieved in the zone of application, as described above, with minimum pressure having to be applied. In addition the degree of compression provides that the element seals with a large variety of configurations of the zone so that it can be used for a large number of different females. It may be necessary to provide a junior-size receiver.

It will be appreciated that the receiver 10 of the invention may be also conveniently used by males, in which case the rim element is not necessary.

In use, according to one embodiment of the invention, when a urine sample is required, a patient will be handed the sterilised receiver, into which the insert 30 containing new dipstick and cellulose sponge has been inserted. The outlet of the receiver will be in the closed position.

The patient will void her/his bladder into the receiver 10, and cover the receiver with the lid 16. The full receiver will be handed to the doctor or nurse, who will be able to see the dipstick through the transparent wall of the receiver 10.

Should further testing be required by a laboratory, the doctor or nurse will attach a sample container 40 to the outlet 19 of the receiver, via the bayonet joint 42, piecing the protective membrane on the sample container and opening the plug 24 in the process. In this manner, the urine drains into the sample container. Once the sample container 40 is full the container is removed from the receiver and the plug is biased back into its closed position by the outlet spring, preventing leakage of excess urine, which may be disposed of into a suitable receptacle when convenient. The sample container is sealed with the rubber stopper lid 44 and sent for further testing.

Figure 7:
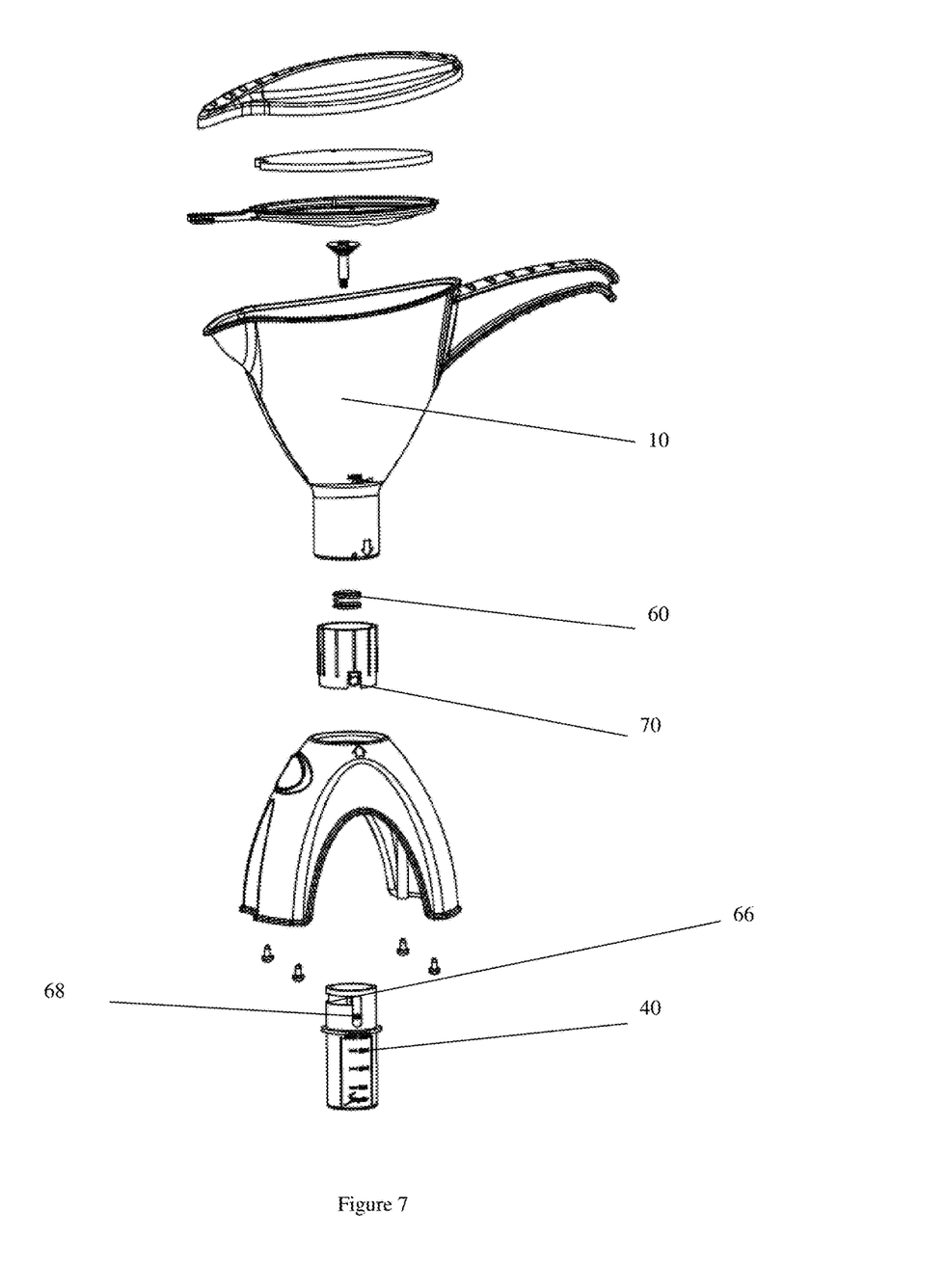
FIG. 7 is an exploded view of a further embodiment of the invention.
Figure 8:
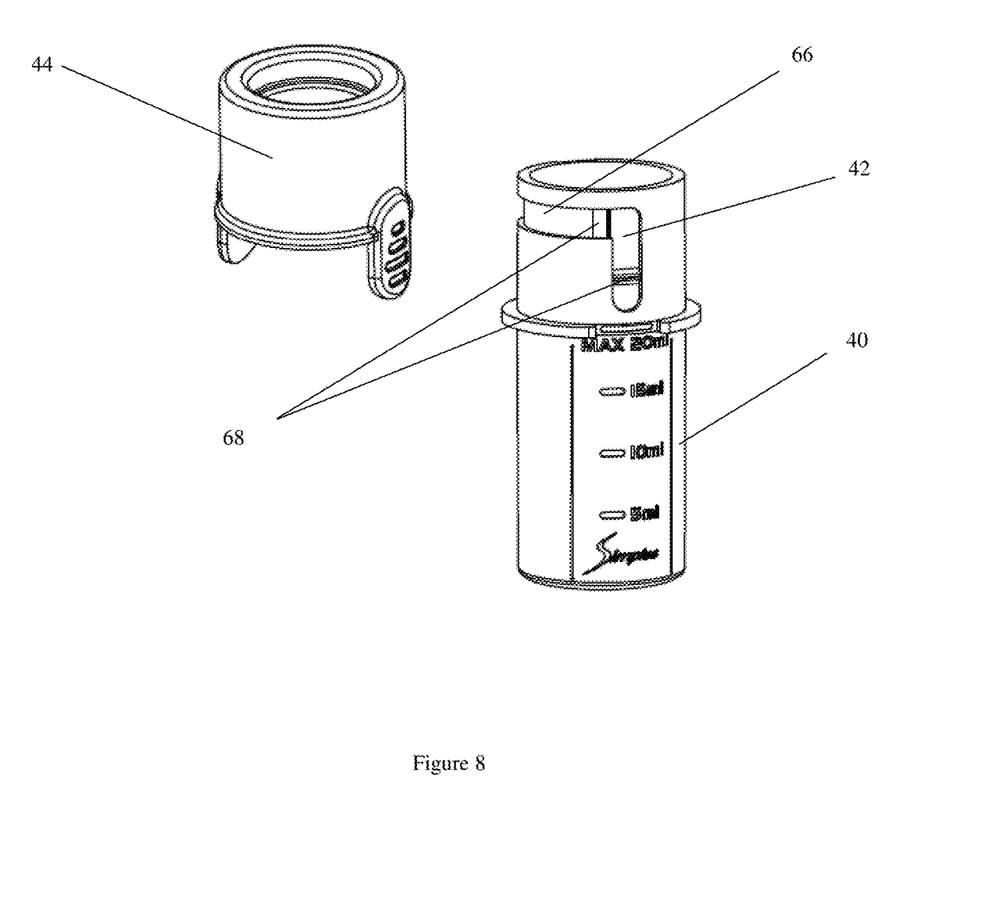
FIG. 8 is a view of a second embodiment of the sample container.

In an embodiment of the invention, as shown in FIGS. 7 and 8, and when in use, the sample container 40 is inserted from the bottom of the receiver 10. Once inserted, the membrane (not shown) is pierced, and this may cause a positive clicking sound which is the protrusions 70 of the receiver 10 engaging the grooves 68 of the channel 70 of the bayonet joint 42. The sample container 40 will then be twisted, which causes the membrane to be cut approximately half way around the opening of the sample container 40. This causes a further positive clicking sound which is the protrusion 70 of the receiver 10 engaging a further groove 68 of the channel 66 of the bayonet joint 42. The sample container 40 is then inserted further into the receiver 10 and the membrane will be cut further. At this stage there is a further positive clicking sound that is heard and felt.

A sample is taken, and the sample container 40 lies at the outlet 19 of the receiver 10. Pressure applied to the sample container 40 allows for the sample container 40 to be filled by the urine collected in the receiver 10. The sample container 40 is pushed against the retractable plug 24 and a spring 60 is activated to allow for the plug 24 to open and urine begins to fill into the sample container 40. When pressure is released, the spring 60 will bias the retractable plug 24 into the original closed position and urine will stop flowing from the receiver 10.

The sample container 40 is then removed by twisting it in the opposite direction as to insertion.

Figure 9:
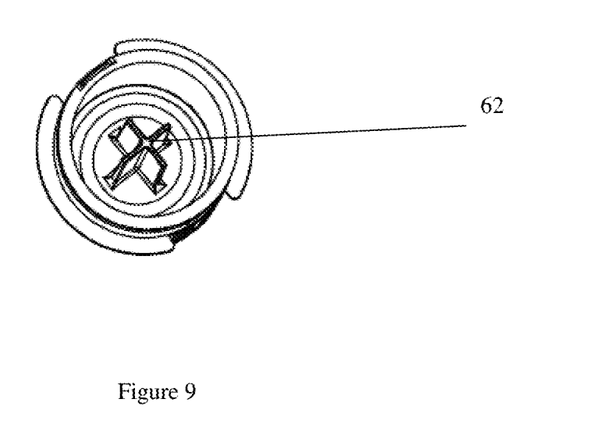
FIG. 9 is a view of the cross member of the sample container.

As shown in FIG. 9, the sample container 40 comprises a cross member 62 which breaks the surface tension of the sample and this prevents any drops from being left behind once the sample container 40 is removed from the receiver 10.

Numerous other embodiments of the invention are possible, for example where the receiver is to be used purely for voiding the bladder in instances where a lavatory is not available, the receiver may be connected to a larger container.

The invention claimed is:

1. A urine receiver comprising a hollow body having an upper end and a lower end,
    the upper end terminating in an open top of saddle shape which at least approximates the configuration of the inside of a users thighs, labia, or other convenient zone,
    the lower end terminating in a base, in which an outlet is located, and configured for discharge of the contents of the receiver, the outlet being connectable to a sample container for collection of samples of urine,
    wherein the urine receiver further comprises an indicator holder for litmus or other indicators, the indicator holder including an insert shaped to support a filter and/or sponge conforming in shape to the inside of the urine receiver, configured for absorbing the initial stream of urine and prevent unwanted ingress of microorganisms or other dirt.

2. The receiver according to claim 1, wherein the receiver includes a handle and a spout for easy disposing of the contents.

3. The receiver according to claim 1, wherein the sample container and the outlet comprise a bayonet joint so that the sample container is easily connected and disconnected to the receiver.

4. The receiver according to claim 3, wherein the bayonet joint comprises one or more protrusions located about an outer circumference of the base of the receiver, on one hand, and a channel formed proximal to the upper end of the sample container, the channel further including one or more transverse grooves.

5. The receiver according to claim 4, wherein the channel includes two transverse grooves.

6. The receiver according to claim 1, wherein the sample container and the outlet are connected by a threaded screw connection.

7. The receiver according to claim 1, wherein the holder comprises channels located along the interior wall of the receiver.

8. The receiver according to claim 1, wherein the sponge is constructed of cellulose or other absorbent material.

9. The receiver according to claim 1, wherein the insert is located just under a spout of the receiver.

10. The receiver according to claim 1, wherein the insert is supported by a ridge extending around an interior of the receiver.

11. The receiver according to claim 1, wherein the insert includes a solid base sloping towards an aperture through which the urine not absorbed by the sponge, may flow.

12. The receiver according to claim 9, wherein the insert includes a suitable spillage protector for the spout.

13. The receiver according to claim 1, wherein the receiver includes a removable support base, on which the receiver may be located when not in use.

14. The receiver according to claim 1, wherein the receiver includes a replaceable rim element adapted to fit the rim and to form a seal with the zone during use.

15. The receiver according to claim 14, wherein the rim element is flexible as well as compressible so that it can seal well with a minimum of pressure being applied.

16. The receiver according to claim 1, wherein the receiver includes a removable lid.

17. A method of collecting urine, using the urine receiver of claim 1, the urine receiver connectable to a sample container comprising a bayonet joint, the method comprising:
    inserting the sample container into an outlet of the urine receiver to a first contact point;
    twisting the sample container to a second contact point;
    inserting the sample container further to a third contact point;
    applying pressure to the sample container to activate a retractable plug held in place by the biasing force of a spring, to an open position; and
    collecting urine which escapes from the urine receiver when the retractable plug is in an open position.

18. The method of claim 17, wherein the retractable plug returns to a closed position when pressure is removed.

19. The method of claim 17, wherein the sample container is removed by twisting it in the opposite direction as to insertion.

20. The receiver according to claim 1, wherein the outlet is closable by a retractable plug, and wherein connection of the sample container to the outlet causes retraction of the plug into an open position, allowing contents of the receiver to drain into the sample container.

* * * * *